(12) United States Patent
Morimoto et al.

(10) Patent No.: US 8,652,833 B2
(45) Date of Patent: Feb. 18, 2014

(54) CELL CULTURE CONTAINER AND METHOD OF PRODUCING THE SAME

(75) Inventors: Yuji Morimoto, Saitama (JP); Taiji Nishi, Okayama (JP); Taisuke Kamada, Ibaraki (JP); Go Tazaki, Ibaraki (JP); Motohiro Fukuda, Ibaraki (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 755 days.

(21) Appl. No.: 12/298,803

(22) PCT Filed: Apr. 25, 2007

(86) PCT No.: PCT/JP2007/059414
§ 371 (c)(1),
(2), (4) Date: Oct. 28, 2008

(87) PCT Pub. No.: WO2007/126127
PCT Pub. Date: Nov. 8, 2007

(65) Prior Publication Data
US 2009/0075363 A1     Mar. 19, 2009

(30) Foreign Application Priority Data

Apr. 28, 2006   (JP) ................................ 2006-124657

(51) Int. Cl.
*C12M 3/00*     (2006.01)
*B05D 5/10*     (2006.01)
*C40B 40/00*    (2006.01)
*C04B 40/02*    (2006.01)

(52) U.S. Cl.
USPC .......... 435/289.1; 427/207.1; 506/13; 506/14

(58) Field of Classification Search
USPC .................. 435/289.1; 427/207.1; 506/13, 14
IPC ..................................... C12M 3/00; B05D 5/10
See application file for complete search history.

(56) References Cited

U.S. PATENT DOCUMENTS 5,108,923 A *   4/1992   Benedict et al. ............... 435/402
6,653,124 B1 *  11/2003  Freeman ..................... 435/297.1
(Continued)

FOREIGN PATENT DOCUMENTS

JP    4-278083    10/1992
JP    7-289234    11/1995
(Continued)

OTHER PUBLICATIONS

Machine translation of Kikuchi et al. (JP 2005-080607).*
(Continued)

*Primary Examiner* — Nathan Bowers
*Assistant Examiner* — Gautam Prakash
(74) *Attorney, Agent, or Firm* — Oblon, Spivak, McClelland, Maier & Neustadt, L.L.P.

(57) ABSTRACT

To provide a cell culture chamber capable of reproducing a cell function in vivo, and a method of producing the same. The cell culture chamber according to the present invention has a concave-convex pattern formed on the surface on which cells are cultured. A concave portion of the concave-convex pattern includes cell culture portions and micro flow channels communicating with the cell culture portions. The bottom surface of each of the cell culture portions has a width 1.0 to 20 times an equivalent diameter of each of the cultured cells. A cell adhesion-inducing substance is formed only on the bottom surface and the side walls of the concave portion.

12 Claims, 14 Drawing Sheets

(56) References Cited

U.S. PATENT DOCUMENTS

| | | |
|---|---|---|
| 2005/0278730 A1 | 12/2005 | Ohgi |
| 2005/0279730 A1 | 12/2005 | Miyabe et al. |
| 2007/0243613 A1 | 10/2007 | Miyake et al. |
| 2010/0330665 A1 | 12/2010 | Miyake et al. |
| 2011/0143439 A1 | 6/2011 | Miyake et al. |

FOREIGN PATENT DOCUMENTS

| | | |
|---|---|---|
| JP | 2003-225083 | 8/2003 |
| JP | 2004-8173 | 1/2004 |
| JP | 2004-154027 | 6/2004 |
| JP | 2005-80607 | 3/2005 |
| JP | 2005-261432 | 9/2005 |
| JP | 2006-223197 | 8/2006 |
| WO | 2006/019043 | 2/2006 |

OTHER PUBLICATIONS

U.S. Appl. No. 12/665,474, filed Dec. 18, 2009, Tazaki, et al.

Motohiro Fukuda, et al., "Micro Patterned Cell Culture Dish", "Nanotechnology MEMS de Shinka suru Saibo Baiyo Manipulation Micro Kukan Saibo Dish", vol. 23, No. 2, Bio Industry, Feb. 12, 2006, pp. 9-13.

Yuji Kikuchi, et al., Micro-channel Array Micro-space Array Gijutsu to Sono Oyo, Chemical Engineering, vol. 51, No. 11, Nov. 1, 2006, pp. 829-836.

U.S. Appl. No. 13/229,087, filed Sep. 9, 2011, Tazaki, et al.

Revised Extended European Search Report for EP Application No. 07 74 2849 mailed Jul. 19, 2012, (5 pp.).

Extended European Search Report for EP application No. 07 74 2849 mailed Apr. 27, 2012.

* cited by examiner

CELL CULTURE CONTAINER AND METHOD OF PRODUCING THE SAME

TECHNICAL FIELD

The present invention relates to a cell culture chamber and a method of producing the same.

BACKGROUND ART

A technique of using cells isolated from a tissue for tests and inspections is essential in biotechnology-related fields. This technique is widely applied to diagnosis of disease and pathology, search for new drugs and determination of drug efficacy, animal inspection, plant inspection, an environmental pollutant test, and so on. Thus, cells and the like used in the biotechnology field have been greatly diversified.

Isolated cells are sometimes used immediately for tests, but in many cases, the cells are cultured in a culture dish or a test tube. Various inspections are carried out using the cultured cells. Cell lines in culture for use in cell culture tests are required to show drug susceptibility and toxic reaction that are similar to those obtained in a test performed in a living body, that is, a so-called in vivo test. In short, it is necessary to form a network of cells regularly arranged on the surface of a cell culture chamber. Furthermore, the cell lines in culture for use in cell culture tests are extremely expensive, so an improvement in survival rate and proliferation rate of cells is desired.

The cell culture tests measure the effect of a drug or the like to be evaluated, by changing its amount, concentration, and the like under the same conditions. For this reason, it is necessary that the cell culture chambers be identical in material, shape, and the like. As the cell culture chambers, a petri dish made of plastic, a petri dish made of glass, a glass plate fixed into a chamber, a well plate, and the like are generally used. Examples of the well plate include 6-well, 12-well, 48-well, and 96-well plates or petri dishes. In general, those plates have substantially the same overall size. As the number of wells increases, the size of a single well becomes smaller. A single well corresponds to a single culture dish. With the recent trend toward miniaturization, a 384-well plate having a number of culture dishes with a small diameter has also come to be used.

However, use of the conventional cell culture chamber for culturing tissue cells causes the cells to be thinned into a form with no orientation. Further, the cells are randomly arranged on the surface of the cell culture chamber, so the networks of cells cross each other in a complicated manner. Thus, there is a problem in that it is impossible to reproduce a cell function in vivo. Possible reasons for this are as follows. That is, although the wells have a small diameter, culture on a cell culture chamber is substantially the same as culture on a flat plate because the size of cells is several micrometers to several tens of micrometers. Furthermore, the cells cannot be regularly arranged because the cells are moved by a culture solution when the cells are arranged using a pipette or the like.

To solve the above-mentioned problems, a method is disclosed in which polylysine or the like, which is a cell adhesion-inducing substance, is coated on the surface on which cells are cultured according to a desired pattern (see Patent Document 1).

[Patent Document 1] Japanese Unexamined Patent Application Publication No. 2004-8173

DISCLOSURE OF THE INVENTION

Problems to be Solved by the Invention

In the method disclosed in Patent Document 1, however, polylysine is coated on the entire surface on which cells are cultured, and then a metal mesh having a line width of 20 μm is deposited thereon as a mask to be irradiated with ultraviolet light, thereby obtaining a pattern of 20 μm to which the ultraviolet light is not applied after cleaning. Thus, there is a problem in that it is necessary to execute complicated steps every time a single plate is produced, which leads to an increase in costs. Furthermore, since the ultraviolet light is applied to each plate to produce a minute polylysine pattern, it is impossible to stably produce the polylysine pattern due to a gap between the metal mesh and polylysine, ultraviolet light irradiation conditions, and cleaning conditions.

The present invention has been made to solve the above-mentioned problems, and it is an object of the present invention to provide a cell culture chamber capable of reproducing a cell function in vivo, a method of producing the same, and a cell culture method.

Means for Solving the Problem

According to the present invention, there is provided a cell culture chamber having a concave-convex pattern formed on a surface on which cells are cultured, in which: a concave portion of the concave-convex pattern includes cell culture portions and micro flow channels communicating with the cell culture portions; a bottom surface of each of the cell culture portions has a width 1.0 to 20 times an equivalent diameter of each of the cultured cells; and a cell adhesion-inducing substance is formed only on the bottom surface and side walls of the concave portion.

According to the present invention, there is provided a method of producing a cell culture chamber having a concave-convex pattern formed on a surface on which cells are cultured, the method including the steps of: forming cell culture portions and micro flow channels communicating with the cell culture portions, the cell culture portions and the micro flow channels being each formed of a concave portion of the concave-convex pattern; and introducing a cell adhesion-inducing substance only to the concave portion by capillarity.

Advantageous Effects of the Invention

According to the present invention, it is possible to provide a cell culture chamber capable of reproducing a cell function in vivo, and a cell culture method.

DESCRIPTION OF REFERENCE NUMERALS

Figure 1A:
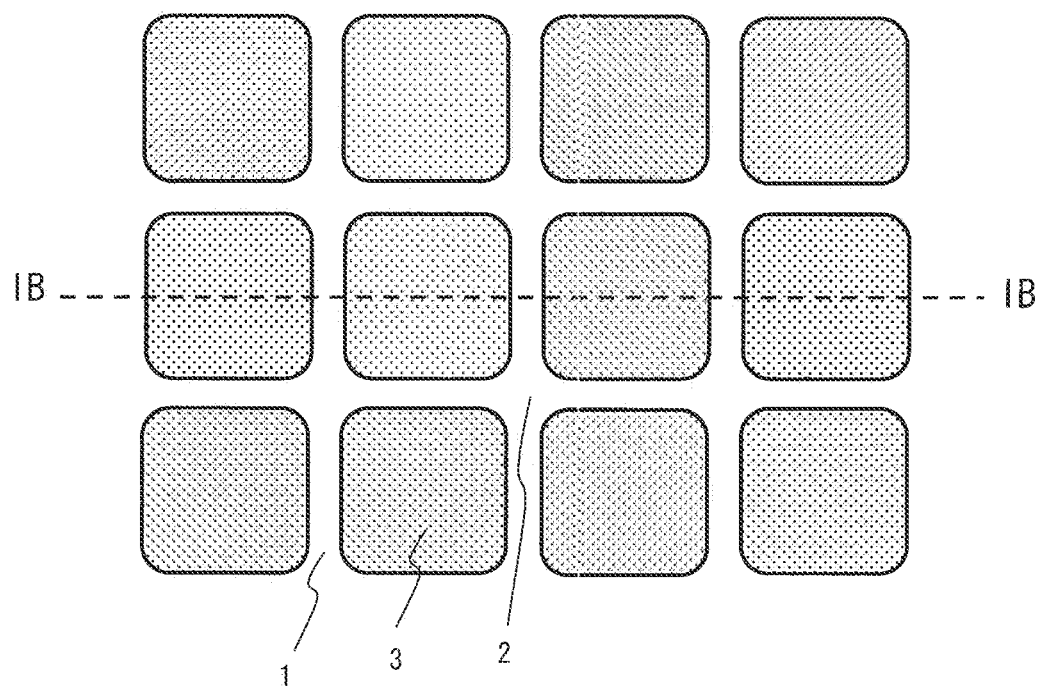
FIG. 1A is a plan view schematically showing the structure of a cell culture chamber according to an embodiment of the present invention.

1 MICRO FLOW CHANNEL
2 CROSSING PORTION
3 CONVEX PORTION
4 MICROCHAMBER
5 INTRODUCTION AREA
11 SUBSTRATE
12 FIRST RESIST LAYER
13 MASK A
14 SECOND RESIST LAYER
15 MASK B
16 RESIST PATTERN
17 CONDUCTIVE FILM
18 METAL STRUCTURE
19 RESIN MOLDED PRODUCT

BEST MODES FOR CARRYING OUT THE INVENTION

As a result of earnest studies, the inventors of the present invention have found it possible to provide a cell culture chamber most suitable for reproducing a cell function in vivo by forming micro flow channels having desired dimensions on the surface, on which cells are cultured (hereinafter, referred to as "culture surface"), of a cell culture chamber such as a plate or a petri dish, and by introducing a liquid containing a cell adhesion-inducing substance to the micro flow channels by utilizing capillarity to thereby increase the density of cells in culture. Embodiments of the present invention will be described below.

In cell culture tests, in general, a cell adhesion-inducing substance such as collagen, laminin, or polylysine is coated on the entire culture surface to promote adhesion/proliferation of cells, and then the cells are arranged thereon. Thus, the cells are randomly arranged on the entire culture surface, and it is impossible to arrange the cells regularly.

The cells that are randomly arranged proliferate and form a plurality of random and complicated networks between neighboring cells or between cells that are apart from each other by 100 μm or more. Accordingly, in the case of observing signal transmission between cells by using a fluorescent probe, for example, the cells contained in a chamber are uniformly stained with the fluorescent probe. Further, a network diameter necessary for the signal transmission becomes smaller, and a fluorescent intensity becomes lower. Accordingly, it is impossible to clarify a mechanism for controlling the order through signal transmission in the network.

The cell culture chamber according to the present invention has micro flow channels formed on the culture surface. When a cell adhesion-inducing substance is introduced to the micro flow channels by utilizing capillarity and dried, the cell adhesion-inducing substance can be coated only on a given portion of the culture surface. Accordingly, the cells are adhered only to the given portion and proliferate. As a result, a regular network of cells like a logic circuit is formed. In other words, a signal transmission model in which a body tissue is reproduced can be realized and applied to studies on a signal transmission process using cultured cells. Also in tests for drug susceptibility and toxicity, the signal transmission model can be applied to studies on the signal transmission process. Since it is possible to control network paths, the network diameter increases, which results in an improvement of the fluorescence intensity. Accordingly, the signal transmission process can be easily observed. Furthermore, by a combination of the present invention with homo culture, hetero culture, a capillary cell sheet, and the like, further development is expected in a regenerative medical technique in the future.

EMBODIMENTS

Hereinafter, embodiments of the present invention will be described. Note that the present invention is not limited to embodiments described below. To clarify the explanation, the following description and the drawings are simplified as appropriate.

Figure 1B:
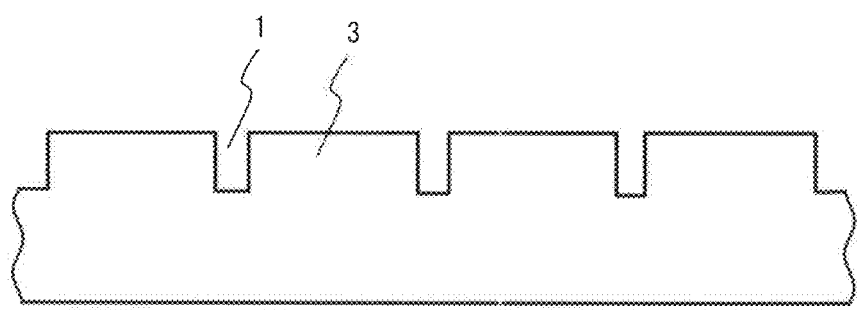
FIG. 1B is a cross-sectional view of FIG. 1A.
Figure 2:
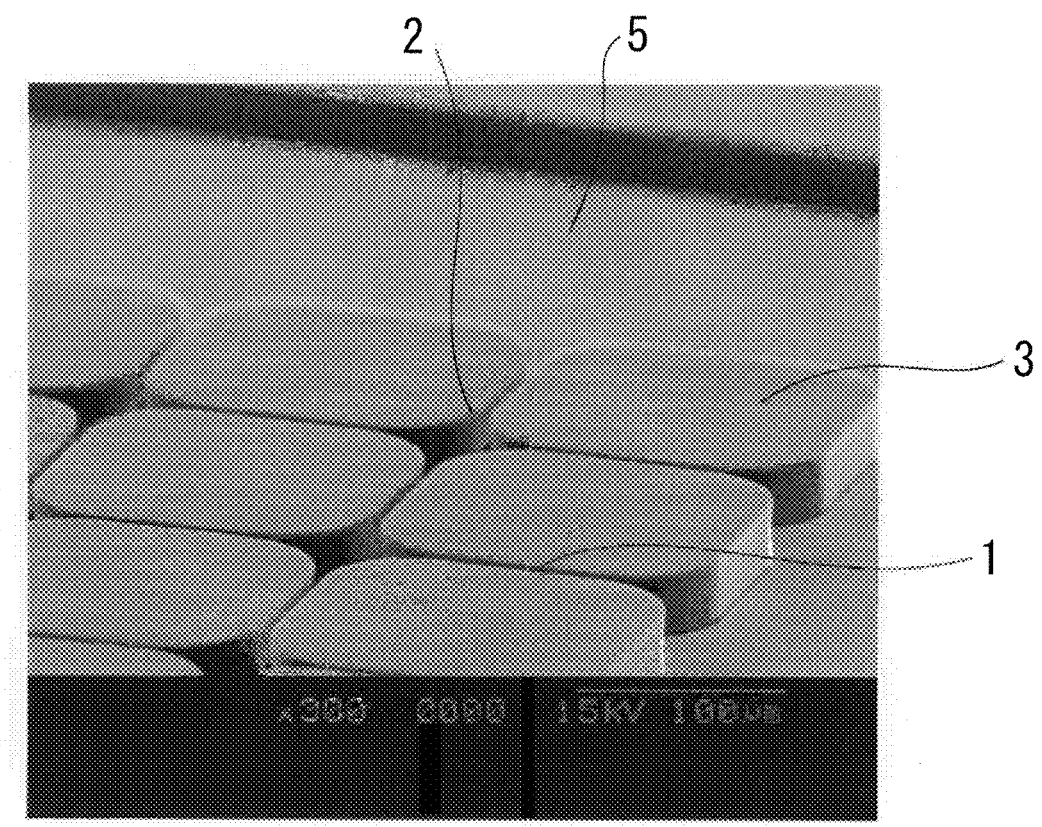
FIG. 2 is an SEM photograph of the cell culture chamber according to an embodiment of the present invention.

Referring to FIGS. 1A, 1B, and 2, the structure of a cell culture chamber according to an embodiment of the present invention will be described. FIG. 1A is a plan view showing the structure of the cell culture chamber according to an embodiment of the present invention. FIG. 1B is a cross-sectional view of FIG. 1A, and FIG. 2 is an SEM photograph (perspective view) thereof.

Referring to FIG. 1A, a plurality of micro flow channels 1 are formed in a net shape on the culture surface of the cell culture chamber. In other words, areas surrounded by rectangular convex portions 3 correspond to the micro flow channels 1. Each of the rectangular convex portions 3 has four rounded vertices obtained by rounding the corners. Alternatively, the convex portions 3 may have a perfect rectangular shape or a shape with chamfered edges. The side walls of the convex portions 3 are formed to be substantially perpendicular to the bottom surface. A liquid containing a cell adhesion-inducing substance is introduced to the micro flow channels 1 and dried, thereby coating the cell adhesion-inducing substance on the micro flow channels. In the cell culture, the cells are arranged and fixed to crossing portions 2 of the micro flow channels 1, and a network of cells is formed along the micro flow channels 1.

The width of each of the micro flow channels 1 formed on the culture surface is preferably 0.1 to 10 times an equivalent diameter of each of the cultured cells. As specific numerical values, the width is preferably within the range of 2 μm to 500 μm, and more preferably within the range of 5 μm to 400 μm. When the width is smaller than 2 μm or larger than 500 μm, the introduction of the liquid containing the cell adhesion-inducing substance is inhibited by capillarity. As a result, it is difficult to form the controlled network. When the width of each of the flow channels becomes larger than 200 μm, a plurality of cells are arranged therein, and the flow channels also function as the chamber for culturing the cells. Even when the plurality of cells are arranged in the micro flow channels 1, a network is formed along the micro flow channels 1, so the network can be used for studies on signal transmission between cells and the like. Furthermore, the width of each of the crossing portions 2 serving as cell culture portions is preferably 1.0 to 20 times the equivalent diameter of each of the cultured cells.

The depth (height of side wall) of each of the micro flow channels 1 is desirably 0.1 to 10 times the equivalent diameter of each of the cultured cells. As specific numerical values, the depth is desirably within the range of 2 μm to 500 μm, and more preferably from 5 μm to 400 μm. When the depth is smaller than 2 μm, it is difficult to introduce the liquid containing the cell adhesion-inducing substance by capillarity, and when the depth is larger than 500 μm, the degree of difficulty in the manufacturing technology increases and the costs also increase.

The opposing micro flow channels 1 are preferably provided at an interval from 5 μm to 150 mm in the lateral and longitudinal directions, and more preferably from 10 μm to 100 mm. When the interval is smaller than 5 μm, the cells can come close to each other without forming a network, so the cells are not suitable for studies on active potential propagation between cells and the like. When the interval exceeds 150 mm, it is difficult to observe a scanning function of cells.

In order to introduce the liquid containing the cell adhesion-inducing substance onto the surface on which the cells are cultured, the liquid can be injected into an end portion of each of the micro flow channels 1 by using a pipette 1 or the like, for example. Alternatively, it is preferable in terms of operation to provide an introduction area 5 formed of a concave portion communicating with at least one of the micro flow channels and to drop the liquid containing the cell adhesion-inducing substance on the introduction area 5. The depth of the micro flow channels 1 may be increased in a stepwise fashion so as to promote the uniform introduction of the liquid containing the cell adhesion-inducing substance into the micro flow channels 1.

When microchambers are provided to the crossing portions 2 of the micro flow channels 1 on the surface on which the cells are cultured, a more advanced network of cells can be formed. For instance, when the width of each of the micro flow channels 1 is set to 10 μm and the width of each of the microchambers is set to be equal to a diameter of 40 μm, the cells are not introduced to the flow channels and are arranged in the microchambers. Then, the network is formed along the micro flow channels 1. The width or diameter of each of the microchambers is preferably within the range of 5 μm to 1000 μm, and more preferably from 10 μm to 500 μm. When the width or diameter is smaller than 5 μm, it is difficult to arrange the cells, and when the width or diameter is larger than 1000 μm, a plurality of cells are randomly adhered in the microchambers, which makes it impossible to form the network into the desired pattern.

The types of the cells to which the cell culture chamber according to the present invention can be applied are not limited, but the present invention is particularly suitable for the types of cells that form a network from neurites of nerve cells and phenochromocytoma (PC12) cells of a rat and a mouse, for example.

In order to set a light transmittance of a resin plate to be equal to that of a glass plate so as to enable observation with transmitted light, the light transmittance at a wavelength within a range of 300 nm to 800 nm including an ultraviolet range is preferably set to be equal to or greater than 80%, and a haze value is preferably set within 10%. To satisfy the above requirements, it is necessary to use, for the cell culture chamber, an acrylic resin excluding an ultraviolet absorber, or to select material not having a ring system in the chemical structure, such as polycarbonate (PC) and polystyrene. Furthermore, it is necessary that additives such as antioxidant, viscosity increasing agent, heat-resistant stabilizer, and agglutination-inhibiting agent do not include the ultraviolet absorber.

In fluorescence observation, if light (excitation light) for exciting fluorescent dye is not transmitted through the cell culture chamber, fluorescence (fluorescent radiation light) generated by the fluorescence observation cannot be recognized. Accordingly, the cell culture chamber is required to have high optical transparency. To obtain the transparency required for recognizing the fluorescence (fluorescent radiation light), a whole light transmittance of 80% or higher and a haze value of 10% or smaller with respect to the visible light are necessary. To satisfy the above requirements, it is preferable to use material excellent in optical property, for example, polymethylmethacrylate. In the case of using a polyolefin resin, it is preferable to use the polyolefin resin in an amorphous state.

Self-fluorescence refers to a phenomenon in which polymer molecules emit fluorescence by itself by emitting light after absorbing ultraviolet/visible light. A glass plate does not emit fluorescence by itself, while many of resin plates emit fluorescence by themselves. For this reason, it is impossible to recognize the fluorescence (fluorescent radiation light) generated from a sample, and thus it is difficult to perform microanalysis which is a feature of fluorescence analysis.

To eliminate the effect of the self-fluorescence, it is necessary to avoid the self-fluorescence by applying light with a wavelength of 230 nm to 800 nm. Accordingly, it is necessary to select, for the cell culture chamber, a resin material not having a ring system in the chemical structure, such as polycarbonate (PC) and polystyrene. Further, to reduce the possibility of occurrence of self-fluorescence as much as possible, it is preferable to use a minimum amount of additives such as antioxidant, viscosity increasing agent, heat-resistant stabilizer, and agglutination-inhibiting agent, or it is preferable not to add such additives.

To perform observation using a polarization microscope or a differential interference microscope without reducing the contrast in differential interference observation, material having less optical strain is required. Accordingly, it is necessary to select, for the cell culture chamber, material not having a ring system in the chemical structure, such as polycarbonate (PC) and polystyrene.

When the cell culture chamber is coated with an organic film or an inorganic film, the cell culture chamber can be made hydrophilic or hydrophobic. As a result, it is possible to prevent air bubbles from being adhered to the microprojections and to control the adhesion degree of cells. For example, a method using low-temperature plasma treatment, corona discharge treatment, violet irradiation, or the like, and a method of applying collagen which is protein promoting the adhesion of cells can be employed. Further, when a part of the cell culture chamber is covered with a mask, only a portion other than the portion covered with the mask can be coated with an organic film or an inorganic film. As a result, it is possible to expand the range of culture test conditions.

Methods of forming an inorganic film, such as a sputtering method and an evaporation method, can be applied to an observation method using an immersion lens. In general, oil used for an immersion lens is mixed with an organic solvent so that optical properties of a glass plate on which cells are cultured can be adapted to those of the optical lens. The organic solvent is immersed into the cell culture chamber made of resin and causes problems of albinism and dissolution, so the organic solvent may be inapplicable. Since an inorganic material has a gas barrier effect as well as resistance to the organic solvent, when an inorganic film is formed on the bottom surface of the cell culture chamber with which the oil of the immersion lens is brought into contact, the inorganic material can be applied to the observation method using the immersion lens, and the applicable range of the cell culture chamber made of resin can be extended. In the case of observation with transmitted light, it is preferable to set the film thickness to be equal to or smaller than 400 nm or to use a transparent inorganic material such as SiO.

A description is given of a method of producing a cell culture chamber including a plurality of microchambers. The production method includes the steps of: forming microspace structures corresponding to microchambers on a substrate; depositing a metal in accordance with a pattern of the micro-space structures formed on the substrate, or a transcription pattern thereof to form a metal structure having a reverse pattern of the structural pattern of a resin plate; and transcribing the pattern of the metal structure to form the resin plate.

In the micro flow channels and microchambers obtained by this method, the resin plate is formed by transcribing the pattern of the metal structure serving as a matrix. As a result, high dimensional accuracy and low costs can be attained. Furthermore, it is only necessary to introduce the cell adhesion-inducing substance into the micro flow channels by utilizing capillarity. Accordingly, a complicated patterning process for forming the cell adhesion-inducing substance is unnecessary.

Details of the method are given below.
(i) Formation of a first resist layer on a substrate
(ii) Alignment between the substrate and a mask A
(iii) Exposure of the first resist layer using the mask A
(iv) Heat treatment of the first resist layer
(v) Formation of a second resist layer on the first resist layer
(vi) Alignment of the substrate and a mask B
(vii) Exposure of the second resist layer using the mask B
(viii) Heat treatment of the second resist layer
(ix) Development of the resist layers The above processes are performed to form a desired resist pattern.
(x) Further, the formed resist pattern is subjected to a conduction process, and a metal structure is then deposited on the substrate by plating in accordance with the formed resist pattern.
(xi) Form a resin molded product with the metal structure being used as a mold.

Thus, the cell culture chamber is produced. The steps (v) to (viii) are optional and can be omitted. Meanwhile, the steps (v) to (viii) can be repeated multiple number of times.

The resist pattern forming process will be described in more detail.

In the case of obtaining a structure having a depth of 30 µm and 100 µm on the substrate, for example, the first resist layer (having a thickness of 70 µm) and the second resist layer (having a thickness of 30 µm) are formed in the stated order, and the exposure or the exposure and heat treatment is carried out on each of the layers. In the development step, a pattern having a depth of 30 µm and serving as the second resist layer is first obtained, and a pattern having a combined depth of 100 µm of the first resist layer and the second resist layer is then obtained. At the time when the pattern having the depth of 100 µm is obtained, in order to prevent the pattern, which has the depth of 30 µm and serves as the second resist layer, from being dissolved or distorted in a developer, it is necessary to control the solubility of each layer in the developer.

One method of developing the alkali resistance of a photodegradable positive resist is to increase a baking time (solvent drying time) so as to harden the resist. In general, the baking time of the resist is set according to the film thickness, the concentration of a solvent such as thinner, and the sensitivity. Increasing the baking time can develop the alkali resistance. Overbaking of the first resist layer hardens the resist too much, which makes it difficult to dissolve a portion irradiated with light and form a pattern in the subsequent development step. Thus, it is preferable to appropriately select baking conditions by reducing the baking time and so on. Equipment used for the baking is not particularly limited as long as it can dry a solvent. An oven, a hot plate, a hot-air dryer, and the like can be employed. Since the development of the alkali resistance is limited compared to a photocrosslinkable negative resist, the combined thickness of the resist layers is preferably within the range of 5 to 200 µm, and more preferably within the range of 10 to 100 µm.

Besides the optimization of the baking time, another method of developing the alkali resistance of the photocrosslinkable negative resist is optimization of crosslink density. In general, the crosslink density of the negative resist can be set according to the exposure amount. In the case of a chemical amplification negative resist, the crosslink density can be set according to the exposure amount and the heat treatment time. The alkali resistance can be developed by increasing the exposure amount or the heat treatment time. In the case of the photocrosslinkable negative resist, the combined thickness of the resist layers is preferably set within the range of 5 to 500 µm, and more preferably within the range of 10 to 300 µm.

(i) The formation of a first resist layer 12 on a substrate 11 will be described.

Figure 3A:
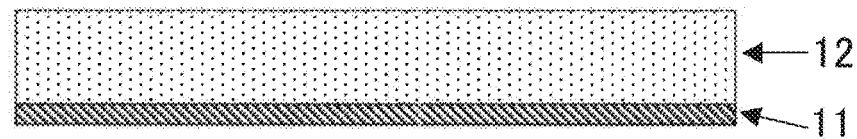
FIG. 3A is a diagram schematically showing a method of producing the cell culture chamber according to an embodiment of the present invention.

FIG. 3A shows a state where the first resist layer 12 is formed on the substrate 11. The flatness of a cell chamber, which is made of resin and obtained by the molded product formation step, is determined by the step of forming the first resist layer 12 on the substrate 11. Thus, the flatness obtained when the first resist layer 12 is formed on the substrate 11 is reflected in the flatness of the metal structure and the cell culture chamber eventually.

Though a method of forming the first resist layer 12 on the substrate 11 is not limited in any way, spin coating, dip coating, roll coating, dry film resist lamination, and the like are generally employed. In particular, the spin coating is a method of applying resist onto a spinning glass substrate, which is advantageous in very flat coating of resist on a glass substrate with a diameter of more than 300 mm. The spin coating is thus preferred for use to achieve high flatness.

Both a positive resist and a negative resist may be used as the first resist layer 12. In either case, the depth of focus on the resist changes depending on the resist sensitivity and exposure conditions. Accordingly, when a UV exposure system is used, for example, it is preferable to select an exposure time and a UV output value according to the thickness and sensitivity of the resist.

If the resist used as the first resist layer 12 is a wet resist, as a method of obtaining a given resist thickness by the spin coating, a method of changing the spin coating rotation speed or a method of adjusting the viscosity may be used, for example. The method of changing the spin coating rotation speed is used for obtaining a given resist thickness by appropriately setting the rotation speed of a spin coater. The method of adjusting the viscosity is used for adjusting the viscosity according to the flatness required for practical use, since there is a fear that the degradation of flatness may occur if the resist is thick or a resist-coated area is large.

In the spin coating, for example, the thickness of the resist layer coated at a time is preferably within the range of 10 to 50 $\mu$m, and more preferably within the range of 20 to 50 $\mu$m, to maintain high flatness. In order to obtain a given resist layer thickness while retaining high flatness, the resist layer may be formed by repeating the forming step a plurality of times.

When the positive resist is used for the first resist layer 12, if a baking time (solvent drying) is extremely long, the resist is excessively hardened, which makes it difficult to form a pattern in the subsequent development step. Thus, it is preferable to appropriately select baking conditions by reducing the baking time and so on if the resist thickness is set to be smaller than 100 $\mu$m.

(ii) The alignment between the substrate 11 and a mask A 13 will be described.

To satisfy a given positional relationship between the pattern of the first resist layer 12 and the pattern of a second resist layer 14 according to a desired design, accurate alignment is necessary at the time of exposure using the mask A 13. Alignment methods include a method of carrying out a cutting operation on the corresponding positions of the substrate 11 and the mask A and fixing them with pins, a method of reading the positions by a laser interferometer, and a method of creating position marks in the corresponding positions of the substrate 11 and the mask A 13 and performing alignment using an optical microscope. In the method of performing alignment using an optical microscope, a position mark is created on the substrate 11 by photolithography technique and a position mark is created on the mask A by a laser exposure system, for example. This method is effective in that the accuracy within 5 $\mu$m can be easily obtained by manual operation using an optical microscope.

(iii) The exposure of the first resist layer 12 with the mask A 13 will be described.

Figure 3B:
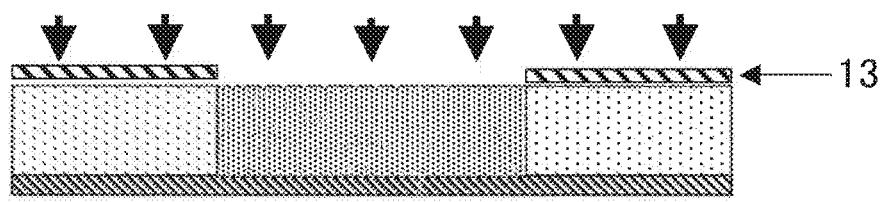
FIG. 3B is a diagram schematically showing the method of producing the cell culture chamber according to an embodiment of the present invention.

The mask A 13 used in the step shown in FIG. 3B is not limited in any way. An emulsion mask, a chrome mask, and the like can be used. In the resist pattern formation step, the size and the accuracy depend on the mask A 13 used. The size and the accuracy are reflected in the cell culture chamber made of resin. Accordingly, to obtain a cell culture chamber made of resin and having a given size and accuracy, it is necessary to specify the size and the accuracy of the mask A 13. A method of increasing the accuracy of the mask A 13 is not limited in any way. For example, one technique is to change a laser light source used for the pattern formation of the mask A 13 to the one with a shorter wavelength. This technique, however, requires high facility costs, which results in higher fabrication costs of the mask A 13. It is thus preferable to appropriately specify the mask accuracy according to the accuracy required for practical use of the cell culture chamber made of resin.

The material of the mask A 13 is preferably quartz glass in terms of temperature expansion coefficient and UV light transmission and absorption characteristics; however, since it is relatively expensive, it is preferable to appropriately select the material according to the accuracy required for practical use of the resin molded product. In order to obtain a desired structure with different depths or heights or a structure in which the first resist pattern and the second resist pattern are different from each other, as designed, it is necessary to ensure the design of the patterns (transmitting/shielding parts) of masks used for the exposure of the first resist layer 12 and the second resist layer 14. An approach to achieve this is to perform simulation using CAE analysis software.

The light source used for the exposure is preferably ultraviolet light or laser light for low facility costs. Synchrotron radiation, which requires high facility costs and thus substantially increases the price of the resin plate, may be used to make deep exposure, for example.

Since exposure conditions such as exposure time and intensity vary depending on the material, thickness, and the like of the first resist layer 12, it is preferable to appropriately adjust the exposure conditions according to the obtained pattern. The adjustment of the exposure conditions is important since the exposure conditions affect particularly the size and the accuracy of a space structure pattern. Further, since the depth of focus changes depending on the resist type, when a UV exposure system is used, for example, it is preferable to appropriately select an exposure time and a UV output value according to the thickness and sensitivity of the resist.

(iv) The heat treatment of the first resist layer 12 will be described.

Heat treatment called annealing is known as the heat treatment after the exposure to correct the shape of the resist pattern. In this case, the heat treatment aims at chemical crosslinking and is carried out only when the chemical amplification negative resist is used. The chemical amplification negative resist is mainly formed of a two- or three-component system. For example, the terminal epoxy group of a chemical structure is ring-opened by exposure light and crosslinking reaction is carried out by the heat treatment. When the film thickness is 100 $\mu$m, for example, the crosslinking reaction progresses in the heat treatment time of several minutes at the set temperature of 100° C.

Excessive heat treatment of the first resist layer 12 makes it difficult to dissolve a non-crosslinked part to form a pattern in the subsequent development step. Thus, if the resist thickness is set to be smaller than 100 µm, it is preferable to appropriately select the operation by reducing the heat treatment time, carrying out the heat treatment only on the second resist layer 14 formed later, and so on.

(v) The formation of the second resist layer 14 on the first resist layer 12 will be described.

Figure 3C:
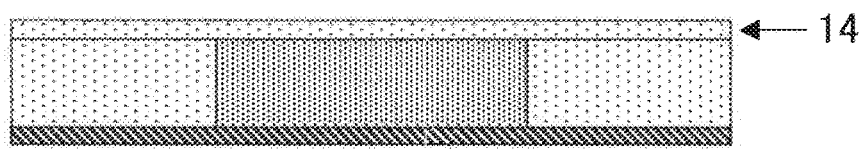
FIG. 3C is a diagram schematically showing the method of producing the cell culture chamber according to an embodiment of the present invention.

FIG. 3C shows a state where the second resist layer 14 is formed. The second resist layer 14 is formed by the same method as the formation of the first resist layer 12 described in the above item (i). In the case of forming the resist layer using a positive resist by spin coating, increasing the baking time about 1.5 to 2 times longer than usual enables development of the alkali resistance. Thus, it is possible to prevent the dissolution or distortion of the resist pattern of the second resist layer 14 at the completion of the development of the first resist layer 12 and the second resist layer 14.

(vi) The alignment between the substrate 11 and a mask B 15 will be described.

The alignment between the substrate 11 and the mask B 15 is performed in the same manner as the alignment between the substrate 11 and the mask A 13 described in the above item (ii).

(vii) The exposure of the second resist layer 14 with the mask B 15 will be described.

Figure 3D:
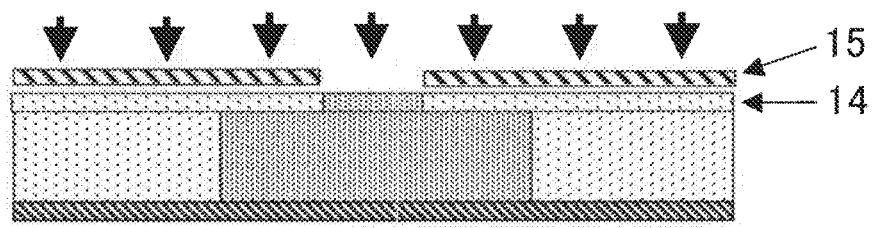
FIG. 3D is a diagram schematically showing the method of producing the cell culture chamber according to an embodiment of the present invention.

The exposure of the second resist layer 14 with the mask B 15 is performed in the same manner as the exposure of the first resist layer 12 with the mask A 13 described in the above item (iii). FIG. 3D shows a state where the second resist layer 14 is subjected to exposure.

(viii) The heat treatment of the second resist layer 14 will be described.

The heat treatment of the second resist layer 14 is performed in the same manner as the heat treatment of the first resist layer 12 described in the above item (iv). The heat treatment of the second resist layer 14 is performed in order to avoid the dissolution or distortion of the pattern of the second resist layer 14 when the pattern of the first resist layer 12 is obtained in the subsequent development step. The heat treatment enhances the chemical crosslinking to increase the crosslink density, thereby developing the alkali resistance. The heat treatment time for developing the alkali resistance is preferably selected according to the resist thickness from the range of 1.1 to 2.0 times longer than usual.

(ix) The development of the second resist layers 12 and 14 will be described.

Figure 3E:
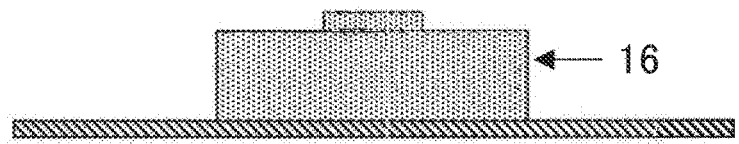
FIG. 3E is a diagram schematically showing the method of producing the cell culture chamber according to an embodiment of the present invention.

In the development step shown in FIG. 3E, it is preferable to use a given developer suitable for the resist used. It is preferable to adjust development conditions such as development time, development temperature, and developer density according to the resist thickness and pattern shape. Setting of appropriate conditions is preferred since overlong development time for obtaining the necessary depth causes the pattern to be larger than a given size, for example. By the development process, a resist pattern 16 is formed.

Examples of the method of increasing the flatness accuracy of the top surface of the cell culture chamber or of the bottom portion of micropatterns include a method of changing the type (negative or positive) of resist used in the resist coating and a method of polishing the surface of a metal structure.

Note that, in the case of forming a plurality of resist layers to obtain a desired mold depth, it is possible to perform the exposure and development of the plurality of resist layers at a time. Alternatively, it is possible to form a resist layer and carry out an exposure process thereon and then additionally form a resist layer and carry out an exposure process thereon, to thereby carry out a development process on two resist layers at a time.

(x) The metal structure formation step will be described in more detail.

The metal structure formation step is a step of depositing a metal over the resist pattern 16 obtained by the resist pattern formation step to form the micro-space structure surface of a metal structure 18 in accordance with the resist pattern 16, thereby obtaining the metal structure 18.

Figure 3F:
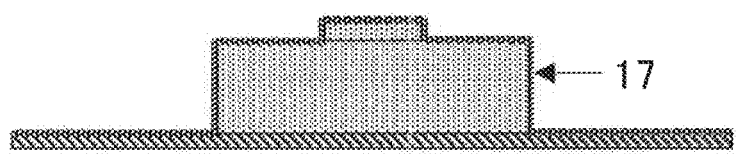
FIG. 3F is a diagram schematically showing the method of producing the cell culture chamber according to an embodiment of the present invention.

As shown in FIG. 3F, a conductive layer 17 is formed in advance in accordance with the resist pattern 16 in this step. Though a method of forming the conductive layer 17 is not particularly limited, it is preferable to employ vacuum evaporation, sputtering, and the like. Examples of the conductive material used for the conductive layer 17 include gold, silver, platinum, copper, and aluminum.

Figure 3G:
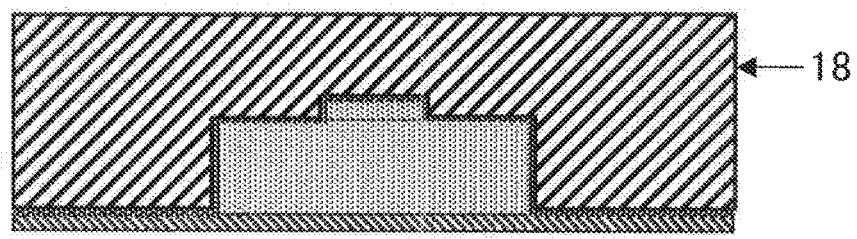
FIG. 3G is a diagram schematically showing the method of producing the cell culture chamber according to an embodiment of the present invention.

As shown in FIG. 3G, after the formation of the conductive film 17, a metal is deposited by plating in accordance with the resist pattern 16, thereby forming the metal structure 18. The plating method is not particularly limited. For example, electrolytic plating and electroless plating can be employed. Though metals to be used are not particularly limited, nickel, nickel and cobalt alloy, copper, or gold may be used, for example. Nickel is preferred since it is less costly and durable.

The metal structure 18 may be polished depending on its surface condition. In this case, there is a fear that a shaped article is contaminated, so it is preferable to perform ultrasonic cleaning after the polishing. Further, it is also possible to perform surface treatment of the metal structure 18 with mold release agent or the like so as to improve the surface condition. Note that an angle of gradient along a depth direction of the metal structure 18 is preferably 50° to 90°, and more preferably, 60° to 87°. The metal structure 18 deposited by plating is separated from the resist pattern 16.

(xi) The molded product formation step will be described in more detail.

Figure 3H:
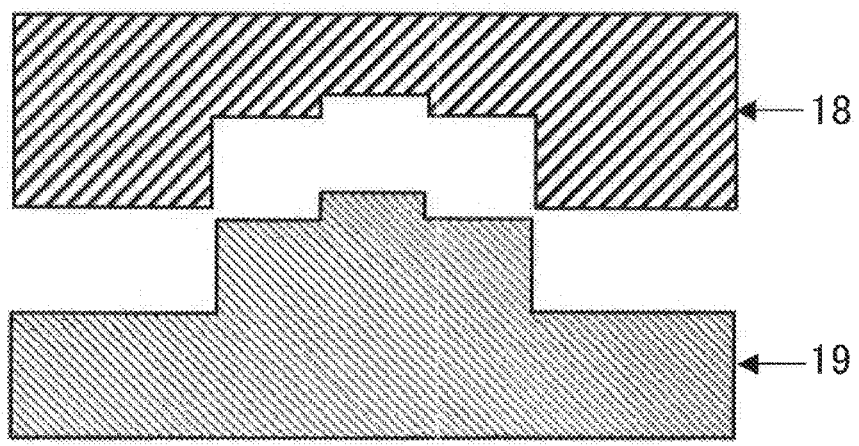
FIG. 3H is a diagram schematically showing the method of producing the cell culture chamber according to an embodiment of the present invention.

The molded product formation step is a step of forming a resin molded product 19 by using the metal structure 18 as a mold as shown in FIG. 3H. Though a method of forming the resin molded product 19 is not particularly limited, injection molding, press molding, monomer casting, solvent casting, or a roll transfer method using extrusion molding may be used, for example. The injection molding is preferred for its high productivity and transcription property. If the resin molded product 19 is formed by the injection molding using the metal structure 18 with a given size as a mold, it is possible to reproduce the shape of the metal structure 18 to the resin molded product 19 with a high transcription rate. Examples of the method of observing the transcription rate include methods using an optical microscope, a scanning electron microscope (SEM), a transmission electron microscope (TEM), or the like.

The minimum value of the flatness of the resin molded product 19 is preferably 1 µm or larger to enable easy industrial reproduction. The maximum value of the flatness of the resin molded product 19 is preferably 200 µm or smaller in order not to cause a problem in the contact between the molded product and an optical system unit due to a warp or the like, for example. The dimensional accuracy of a shaped portion of the resin molded product is preferably within the range of ±0.5 to 10% to enable easy industrial reproduction.

Examples and comparative examples according to the present invention are shown below. In these examples and comparative examples, the degree of network formation and cell excitability of rat brain hippocampal neurons and phenochromocytoma (PC12) cells were evaluated by varying the dimensions of the micro flow channels of the cell culture chamber. Optical properties such as a whole light transmittance and a haze value were measured using a visible light transmittance meter (type: HA-TR) produced by SUGA TEST instruments CO., LTD. Specifically, the whole light transmittance was measured twice by a method compliant with JIS K6714, thereby obtaining the average value. Further, the thickness of a deposition film was measured by a stylus method using a surface profile measuring system (DEKTAK 3030) produced by ULVAC, Inc.

The cell adhesion-inducing substance is introduced in the following manner. In the comparative examples, the surface on which the cells were cultured was immersed in the liquid containing the cell adhesion-inducing substance, and was then dried for six hours. In the examples, the liquid containing the cell adhesion-inducing substance was dropped on the introduction area 5 by using a pipette and was introduced only to the micro flow channels and to the side walls and lower part of each of the microchambers by capillarity, and was then dried for six hours. As the liquid containing the cell adhesion-inducing substance, polylysine+laminin was used for brain hippocampal neurons, and collagen I was used for phenochromocytoma cells.

In both cases, $2.0 \times 10^4$ of cells were dispersed. The brain hippocampal neurons were cultured for 10 days after the dispersion of the cells. Two days after the dispersion of the PC12 cells, a nerve growth factor was added, and the cells were further cultured for 10 days.

The degrees of cell network formation were observed using an inverted microscope (TE2000-PFS) produced by Nikon Corporation. The evaluation was performed by classifying the degrees of cell network formation into categories such as "o" (network formation), "Δ" (partial formation), and "x" (random network).

As for the active state (cell excitability) in the cell network formation, $Ca^{2+}$ dynamics were measured and analyzed using $Ca^{2+}$ sensitive fluorescent dye (type: Fluo-4) produced by Dojindo Laboratories. The analysis was performed using a ratio imaging system (AQUACOSMOS/RATIO) produced by Hamamatsu Photonics K.K., and the evaluation was performed by classifying the dynamics into grades of 0, $1^+$ to $4^+$ based on a difference in stainability of the network.

Comparative Example 1

A commercially-available sterilized petri dish (90 mm in diameter and 20 mm in depth) made of polystyrene was used.

As optical properties, a whole light transmittance of 84% and a haze value of 4.3% were obtained.

Comparative Example 2

Figure 4A:
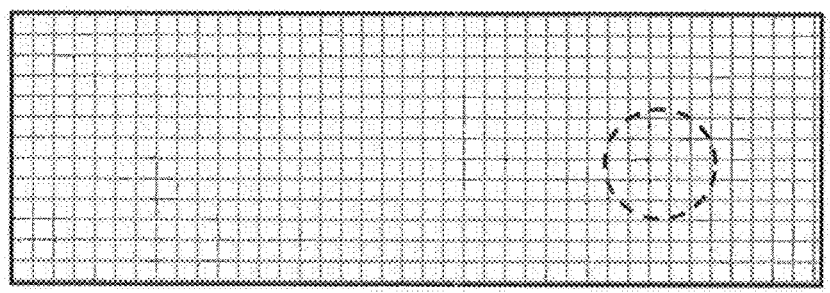
FIG. 4A is a plan view schematically showing a cell culture chamber according to Comparative Example 2.
Figure 4B:
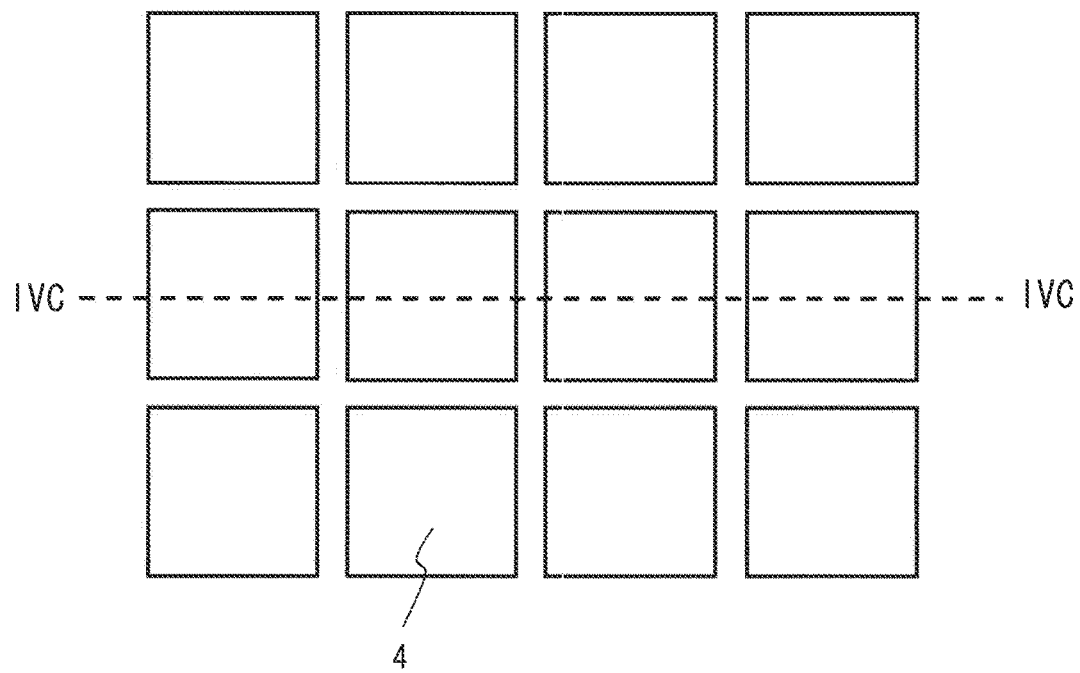
FIG. 4B is an enlarged view of a portion indicated by a broken line circle of FIG. 4A.
Figure 4C:
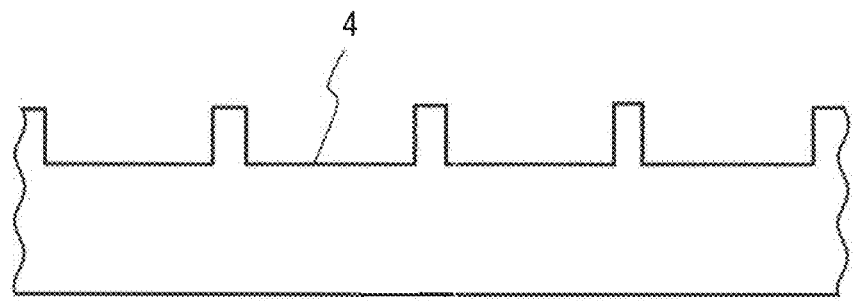
FIG. 4C is a cross-sectional view of FIG. 4B.

By using an acrylic resin (parapet GH-S) produced by KURARAY CO., LTD., a plate having a plurality of microchambers 4 with a length and a width of 50 μm and a depth of 30 μm as shown in FIGS. 4B and (c) was produced on a resin plate having a width of 24 mm, a length of 74 mm, and a thickness of 1.0 mm as shown in FIG. 4A by injection molding using a stamper. The microchambers 4 are provided at an interval of 15 μm in the lateral and longitudinal directions. FIG. 4B is an enlarged view of a portion indicated by a broken line circle of FIG. 4A, and is also a plan view schematically showing the structure of a cell culture chamber according to Comparative Example 2. FIG. 4C is a cross-sectional view of FIG. 4B.

Next, to prevent mixing of air bubbles into the microchambers, an oxidized silicon ($SiO_2$) film having a thickness of 0.2 μm was formed using an evaporation system (type: UEP) produced by ULVAC, Inc. After that, the film was sterilized.

As optical properties, a whole light transmittance of 83% and a haze value of 8.2% were obtained.

Example 1

Figure 5A:
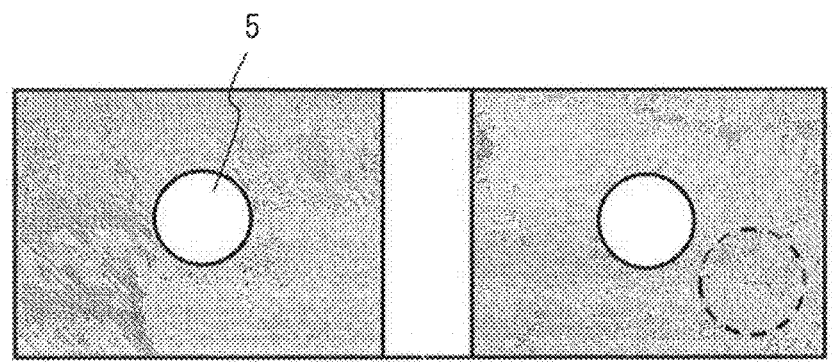
FIG. 5A is a plan view schematically showing a cell culture chamber according to Example 1 of the present invention.
Figure 5B:
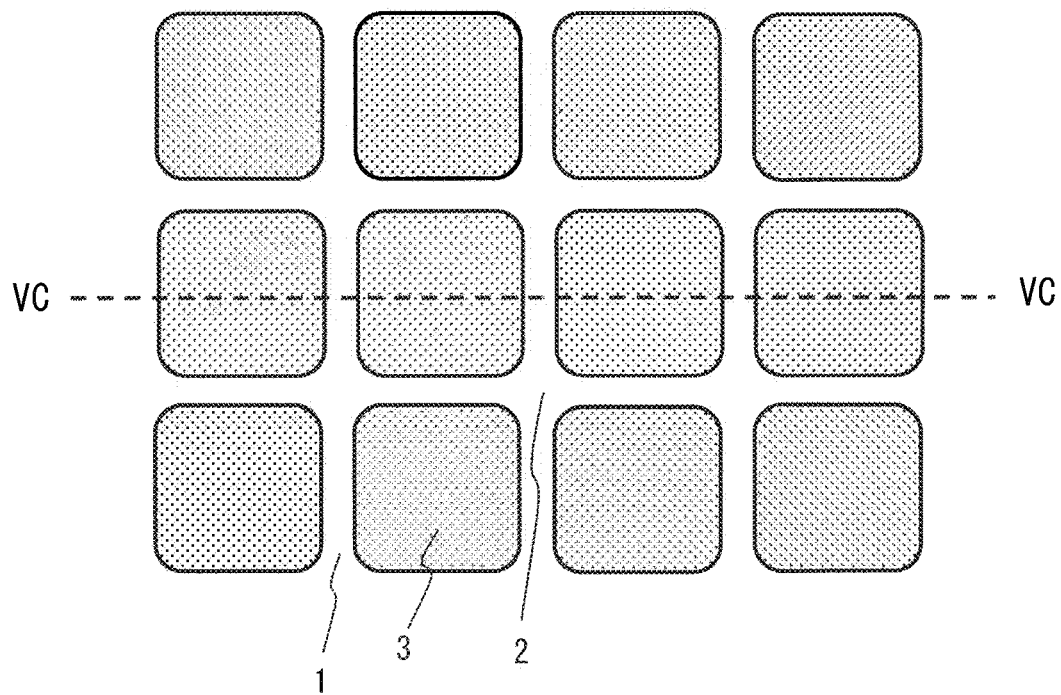
FIG. 5B is an enlarged view of a portion indicated by a broken line circle of FIG. 5A.
Figure 5C:
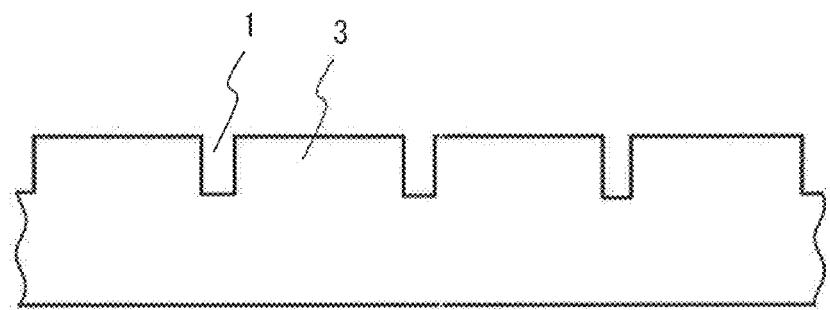
FIG. 5C is a cross-sectional view of FIG. 5B.

By using an acrylic resin (parapet GH-S) produced by KURARAY CO., LTD., a plate having the micro flow channels 1, which have a width of 20 μm and a depth of 30 μm and which are provided at an interval (width of convex portion 3) of 180 μm in the lateral and longitudinal directions, and having two introduction areas 5, which have a diameter of 4 mm for introducing the liquid containing the cell adhesion-inducing substance, as shown in FIGS. 5B and (c), was produced on a resin plate having a width of 24 mm, a length of 74 mm, and a thickness of 1.0 mm as shown in FIG. 5A by injection molding using a stamper. The introduction areas 5 are concave portions that are one step lower than the micro flow channels 1. FIG. 5B is an enlarged view showing a portion indicated by a broken line circle of FIG. 5A, and is also a plan view schematically showing the structure of a cell culture chamber according to Example 1.

Next, to prevent mixing of air bubbles into the micro flow channels 1, an oxidized silicon ($SiO_2$) film having a thickness of 0.3 μm was formed using an evaporation system (type: UEP) produced by ULVAC, Inc. After that, the film was sterilized.

As optical properties, a whole light transmittance of 87% and a haze value of 9.7% were obtained.

Example 2

Figure 6A:
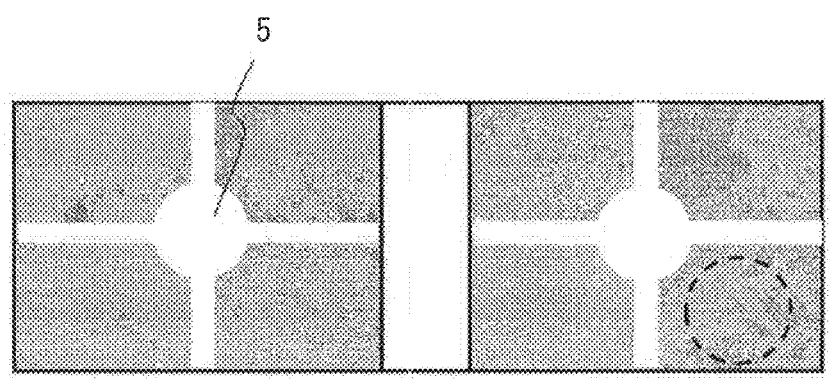
FIG. 6A is a plan view schematically showing a cell culture chamber according to Example 2 of the present invention.
Figure 6B:
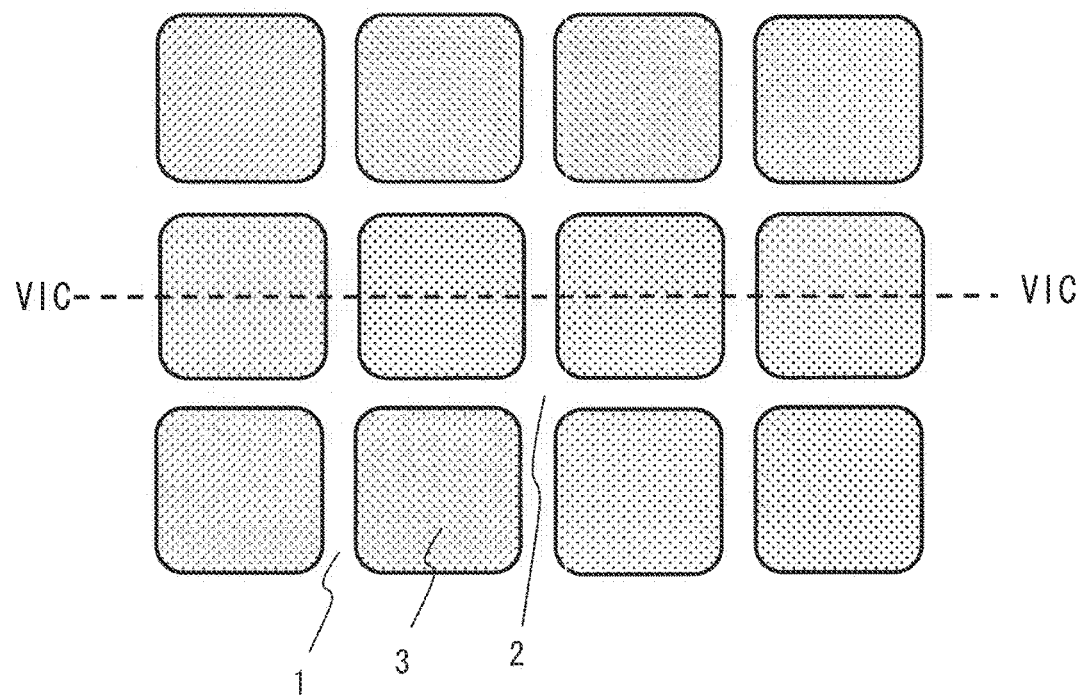
FIG. 6B is an enlarged view of a portion indicated by a broken line circle of FIG. 6A.
Figure 6C:
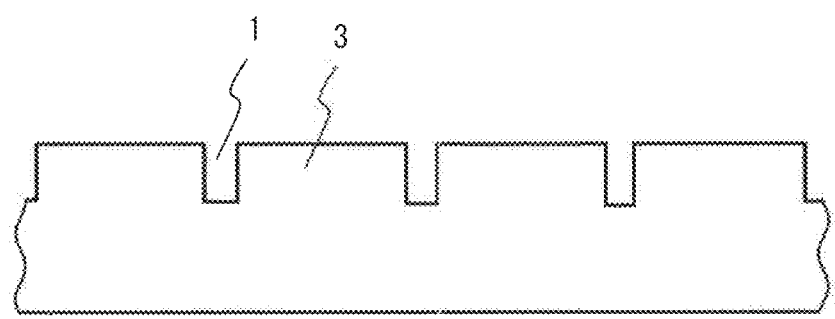
FIG. 6C is a cross-sectional view of FIG. 6B.

By using an acrylic resin (parapet GH-S) produced by KURARAY CO., LTD., a plate having the micro flow channels 1, which have a width of 20 μm and a depth of 50 μm and which are provided at an interval (width of convex portion 3) of 280 μm in the lateral and longitudinal directions, and having two introduction areas 5, which have a diameter of 4 mm for introducing the liquid containing the cell adhesion-inducing substance, as shown in FIGS. 6B and 6C, was produced on a resin plate having a width of 24 mm, a length of 74 mm, and a thickness of 1.0 mm as shown in FIG. 6A by injection molding using a stamper. The introduction areas 5 are concave portions that are one step lower than the micro flow channels 1. Further, the concave portions are formed in a cross shape with the two introduction areas 5 as a center, so the entire plate is easily filled with the liquid containing the cell adhesion-inducing substance. FIG. 6B is an enlarged view of a portion indicated by a broken line circle of FIG. 6A, and is also a plan view schematically showing the structure of a cell culture chamber according to Example 2. FIG. 6C is a cross-sectional view of FIG. 6B.

Next, to prevent mixing of air bubbles into the micro flow channels 1, an oxidized silicon ($SiO_2$) film having a thickness of 0.3 μm was formed using an evaporation system (type: UEP) produced by ULVAC, Inc. After that, the film was sterilized.

As optical properties, a whole light transmittance of 88% and a haze value of 5.2% were obtained.

Example 3

Figure 7A:
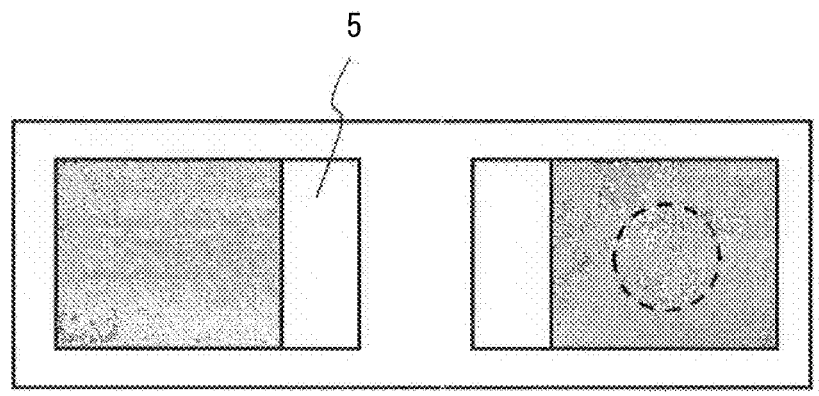
FIG. 7A is a plan view schematically showing a cell culture chamber according to Example 3 of the present invention.
Figure 7B:
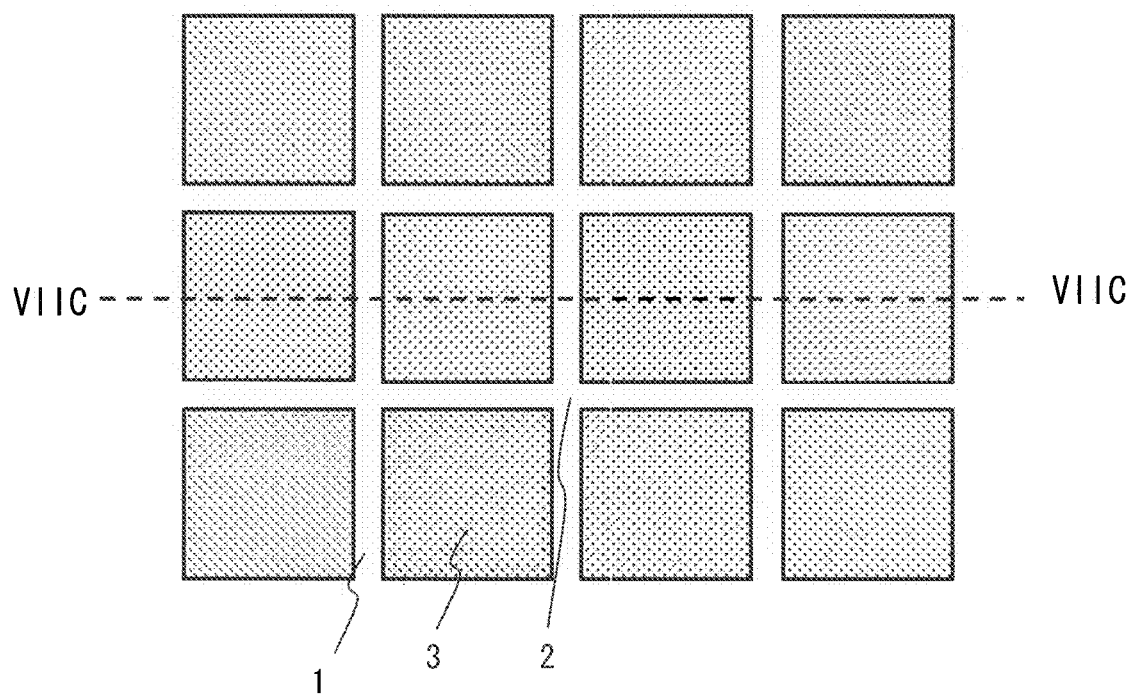
FIG. 7B is an enlarged view of a portion indicated by a broken line circle of FIG. 7A.
Figure 7C:
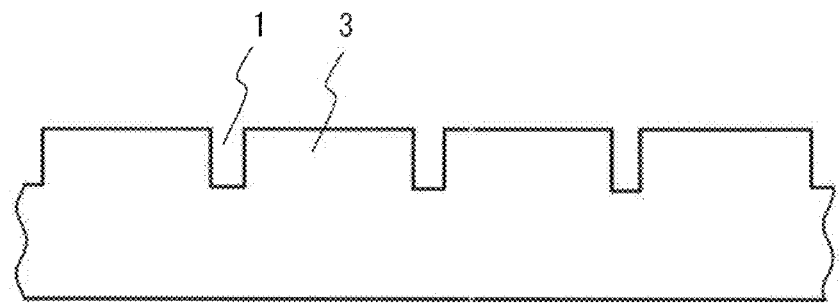
FIG. 7C is a cross-sectional view of FIG. 7B.

By using an acrylic resin (parapet GH-S) produced by KURARAY CO., LTD., a plate having the micro flow channels 1, which have a width of 25 μm and a depth of 50 μm and which are provided at an interval (width of convex portion 3) of 275 μm in the lateral and longitudinal directions, and having two introduction areas 5 having dimensions of 4 mm×20 mm for introducing the liquid containing the cell adhesion-inducing substance, as shown in FIGS. 7B and 7C, was produced on a resin plate having a width of 24 mm, a length of 74 mm, and a thickness of 1.0 mm as shown in FIG. 7A by injection molding using a stamper. The introduction areas 5 are concave portions that are one step lower than the micro flow channels 1. FIG. 7B is an enlarged view of a portion indicated by a broken line circle of FIG. 7A, and is also a plan view schematically showing the structure of a cell culture chamber according to Example 3. FIG. 7C is a cross-sectional view of FIG. 7B.

Next, to prevent mixing of air bubbles into the micro flow channels 1, an oxidized silicon ($SiO_2$) film having a thickness of 0.3 μm was formed using an evaporation system (type: UEP) produced by ULVAC, Inc. After that, the film was sterilized.

As optical properties, a whole light transmittance of 89% and a haze value of 4.2% were obtained.

Example 4

Figure 8A:
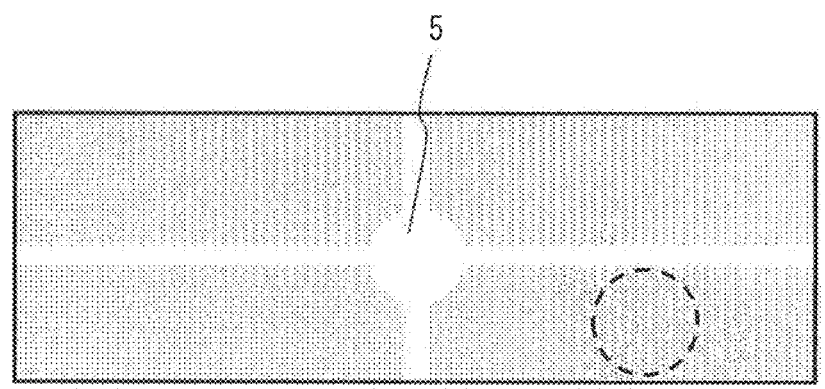
FIG. 8A is a plan view schematically showing a cell culture chamber according to Example 4 of the present invention.
Figure 8B:
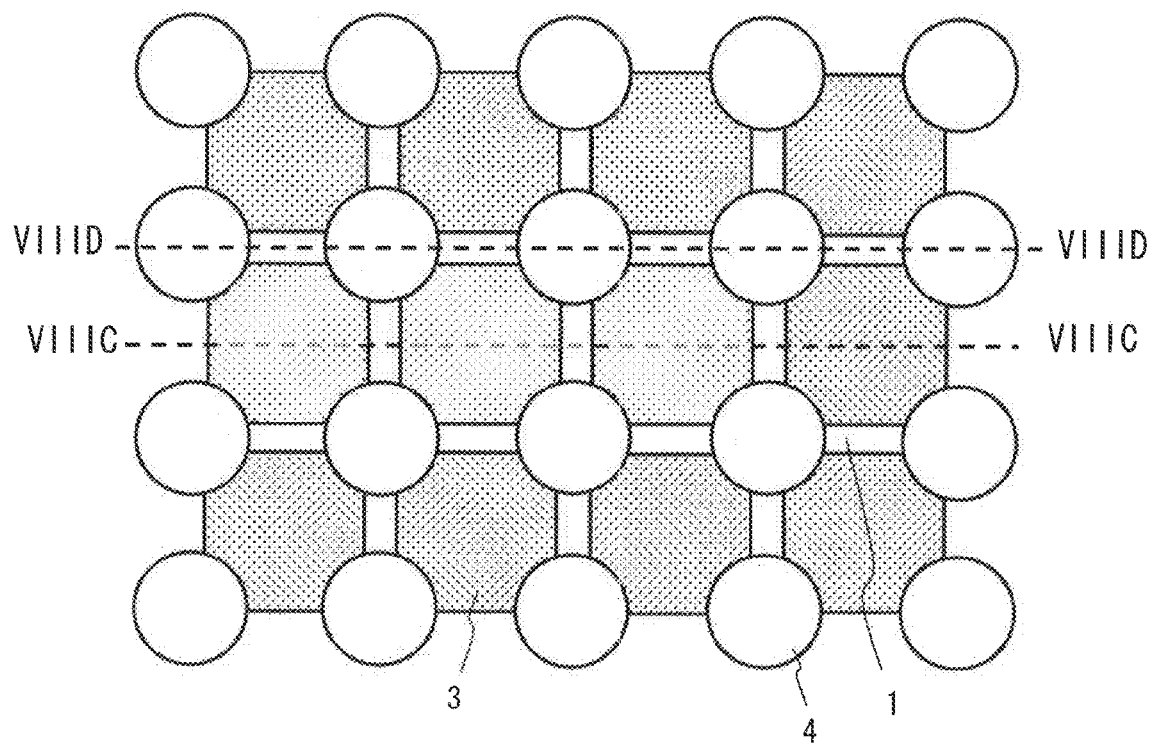
FIG. 8B is an enlarged view of a portion indicated by a broken line circle of FIG. 8A.
Figure 8C:
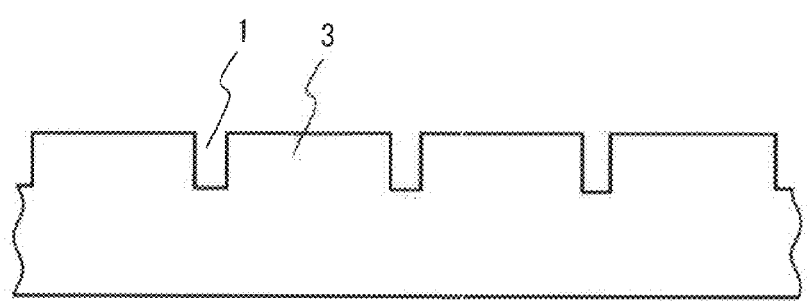
FIG. 8C is a cross-sectional view of FIG. 8B.
Figure 8D:
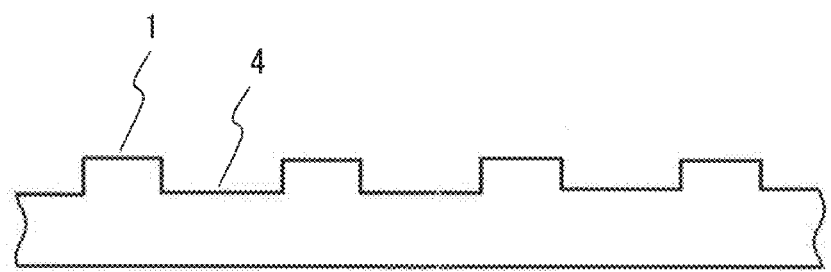
FIG. 8D is a cross-sectional view of FIG. 8B.

By using an acrylic resin (parapet GH-S) produced by KURARAY CO., LTD., a plate as shown in FIGS. 8B and (c) was produced on a resin plate having a width of 24 mm, a length of 74 mm, and a thickness of 1.0 mm as shown in FIG. 8A by injection molding using a stamper. The plate includes: the micro flow channels 1, which have a width of 10 μm and a depth of 30 μm and which are provided at an interval (width of convex portion 3) of 190 μm in the lateral and longitudinal directions; one introduction area 5 having a diameter of 10 mm for introducing the liquid containing the cell adhesion-inducing substance; and the microchambers 4 which have a diameter of 40 μm and a depth of 20 μm and which are each provided at the crossing portion 2 of the micro flow channels 1. The introduction areas 5 are concave portions that are one step lower than the micro flow channels 1. Further, the concave portions are formed in a cross shape with the introduction area 5 as a center, so the entire plate is easily filled with the liquid containing the cell adhesion-inducing substance. FIG. 8B is an enlarged view showing a portion indicated by a broken line circle of FIG. 8A, and is also a plan view schematically showing the structure of a cell culture chamber according to Example 4. FIG. 8C is a cross-sectional view taken along the line VIIIC-VIIIC of FIG. 8B, and FIG. 8D is a cross-sectional view taken along the line VIIID-VIIID of FIG. 8B. Since the microchambers 4 are positioned on the lower side of the micro flow channels 1 as shown in FIG. 8D, the liquid containing the cell adhesion-inducing substance is easily introduced to the microchambers 4.

Next, to prevent mixing of air bubbles into the micro flow channels 1, an oxidized silicon ($SiO_2$) film having a thickness of 0.3 μm was formed using an evaporation system (type: UEP) produced by ULVAC, Inc. After that, the film was sterilized.

As optical properties, a whole light transmittance of 89% and a haze value of 6.5% were obtained.

Table 1 collectively shows culture results of the rat hippocampal neurons and the phenochromocytoma (PC12) cells according to the above comparative examples and examples.

TABLE 1

| | Dimensions of flow channel (μm) | | Dimensions of chamber (μm) | | Optical properties (%) | | Network of rat hippocampal neurons | | Network of phenochromocytoma (PC12) cells | |
|---|---|---|---|---|---|---|---|---|---|---|
| | Width | Depth | Width | Depth | Transmittance | Haze | Degree of formation | Cell excitability | Degree of formation | Cell excitability |
| Comparative Example 1 | — | — | — | — | 84 | 4.3 | x | 1 | x | 1 |
| Comparative Example 2 | — | — | 50 | 30 | 83 | 8.2 | x | 1 | x | 1 |
| Example 1 | 20 | 30 | — | — | 87 | 9.7 | Δ | 2 | Δ~○ | 3 |
| Example 2 | 20 | 50 | — | — | 88 | 5.2 | ○ | 4 | ○ | 4 |
| Example 3 | 25 | 50 | — | — | 89 | 4.2 | ○ | 4 | ○ | 3 |
| Example 4 | 10 | 30 | 40 | 20 | 89 | 6.5 | ○ | 4 | ○ | 4 |

Figure 9:
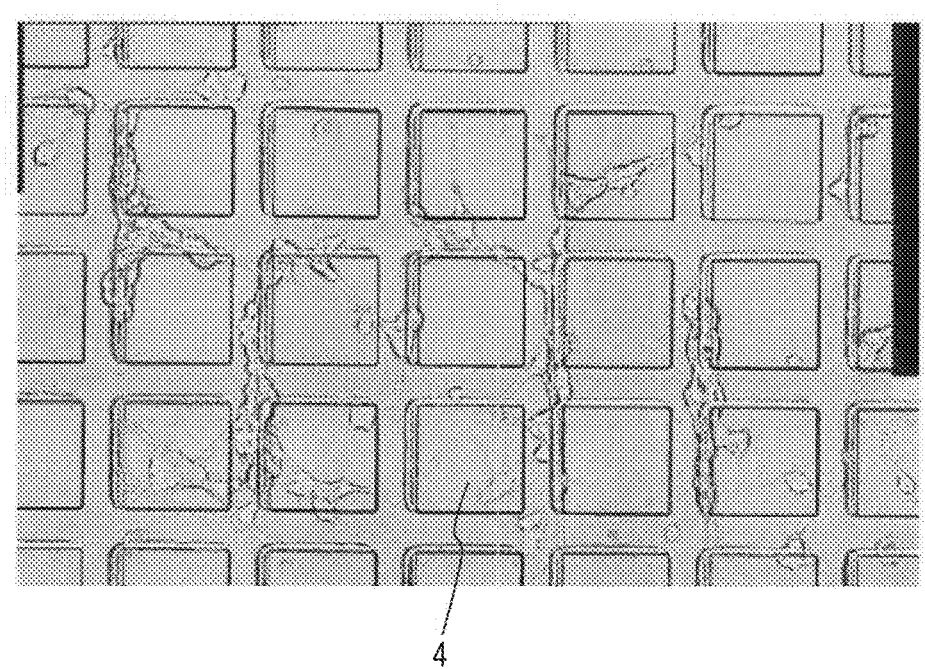
FIG. 9 is a photograph of phenochromocytoma (PC12) cells obtained after 10-day culture according to Comparative Example 2.

In the comparative examples in which the micro flow channels 1 were not provided, the cells were not able to form a regular network. Further, since the network diameter is small, the cell excitability is also lower than that of the examples. In Comparative Example 2 in which only the microchambers 4 were provided, the cell adhesion-inducing substance was coated on the entire culture surface. As a result, the cells crossed over the walls of the microchambers and formed a random network. FIG. 9 shows a photograph of phenochromocytoma (PC12) cells which are obtained after the cells are cultured for 10 days in the cell culture chamber according to Comparative Example 2 and which are observed with a microscope.

Figure 10A:
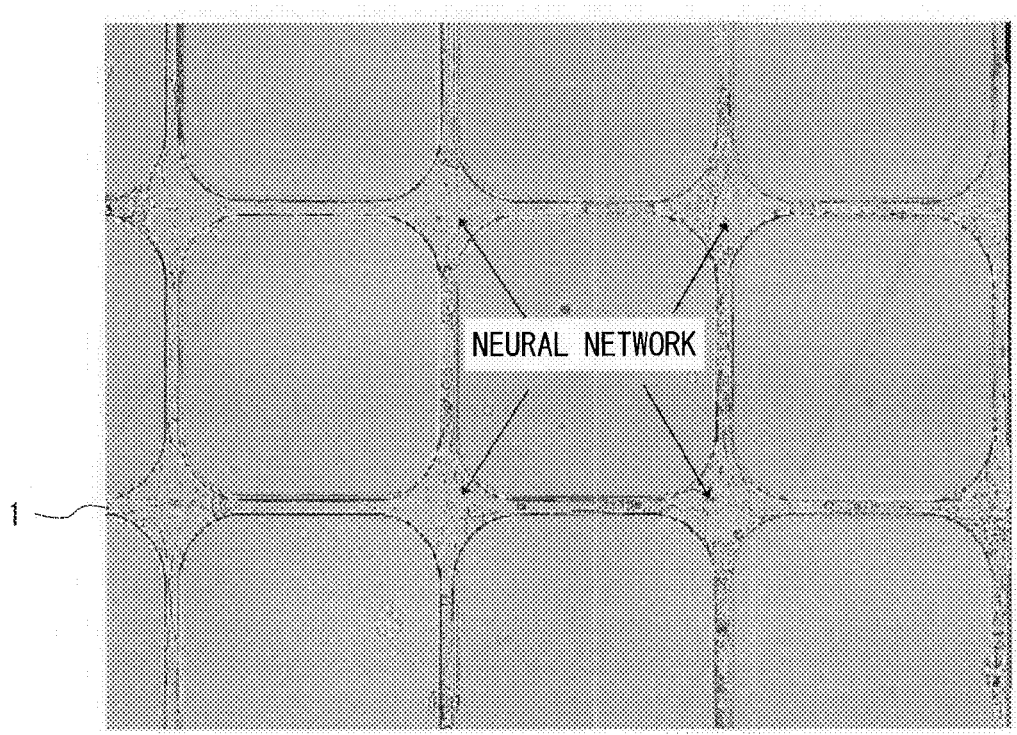
FIG. 10A is a photograph of phenochromocytoma (PC12) cells obtained after 10-day culture according to Example 1.
Figure 10B:
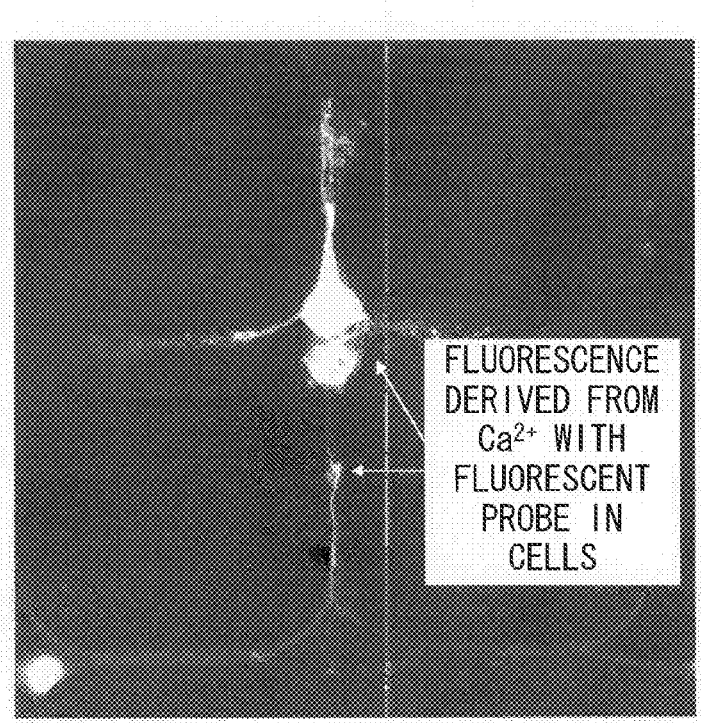
FIG. 10B is a photograph of phenochromocytoma (PC12) cells obtained after 10-day culture according to Example 1.

On the other hand, since the micro flow channels 1 were provided in the examples, the liquid containing the cell adhesion-inducing substance was introduced only to the micro flow channels 1 by capillarity. As a result, the cells can form an advanced network without crossing over the walls of the micro flow channels 1. When the depth of each of the micro flow channels 1 is set to be larger than 30 μm of Example 2, the cell adhesion-inducing substance can be reliably introduced only to the flow channels, and the network of a high degree of completion can be formed. Further, since the diameter of the network becomes larger, the cell excitability is also higher than that of the comparative examples. Furthermore, the examples are excellent in all aspects of transparency, network formation, and cell excitability, and are particularly suitable for the observation of cells with transmitted light. FIG. 10 show a photograph (FIG. 10A) of the phenochromocytoma (PC12) cells which are obtained after the cells are cultured for 10 days in the cell culture chamber according to Example 1 and which are observed with a microscope, and show a fluorescent image (FIG. 10B) thereof derived from $Ca^{2+}$ with a fluorescent probe in the cells.

INDUSTRIAL APPLICABILITY

The present invention is applicable to, for example, cell culture chambers for use in culture of cells isolated from a tissue for tests and inspections.

The invention claimed is:

1. A method of producing a cell culture chamber having a concave-convex pattern formed on a surface on which cells are cultured, the method comprising the steps of:
    forming cell culture portions, micro flow channels communicating with the cell culture portions, and an introduction area communicating with the cell culture portions through the micro flow channels, the cell culture portions, the micro flow channels, and the introduction area being each formed of a concave portion of the concave-convex pattern;
    dropping a liquid containing a cell adhesion-inducing substance on the introduction area so as to introduce the liquid only to the concave portion of the micro flow channels and subsequently to the cell culture portions by capillarity; and
    drying the liquid introduced to the concave portion so as to coat the cell adhesion-inducing substance to the concave portion of the microflow channels and cell culture portions;
    wherein said micro flow channels have a width ranging from 1 µm to 500 µm and a depth ranging from 2 µm to 500 µm; and
    wherein the cell culture portions have a width ranging from 5 µm to 1,000 µm.

2. The method of producing a cell culture chamber according to claim 1, wherein the concave portion is subjected to surface treatment, and the cell adhesion-inducing substance is introduced onto the concave portion.

3. The method of producing a cell culture chamber according to claim 2, wherein the surface treatment is hydrophilic treatment.

4. The method of claim 1, comprising forming cell culture portions having a width or diameter ranging from 10 µm to 500 µm.

5. The method of claim 1, comprising forming micro flow channels communicating with the cell culture portions having a width and depth ranging from 5 µm to 400 µm.

6. The method of claim 1, comprising forming micro flow channels at intervals of 5 µm to 150 mm in the lateral and longitudinal directions of the cell culture chamber.

7. The method of claim 1, comprising forming micro flow channels at intervals of 10 µm to 100 mm in the lateral and longitudinal directions of the cell culture chamber.

8. The method of claim 1,
    comprising forming cell culture portions that are microchambers having a width or diameter ranging from 10 µm to 500 µm,
    comprising forming micro flow channels communicating with the cell culture portions having a width and depth ranging from 5 µm to 400 µm, and
    comprising forming micro flow channels at intervals of 10 µm to 100 mm in the lateral and longitudinal directions of the cell culture chamber.

9. The method of claim 1, wherein the cell adhesion-inducing substance is collagen.

10. The method of claim 1, wherein the cell adhesion-inducing substance is laminin or polylysine.

11. The method of claim 1, further comprising cultivating cells in the cell culture portions of the cell culture chamber.

12. The method of claim 11, wherein the cultivated cells have diameters ranging from 0.1 to 10 times the diameter of the micro flow channels.

* * * * *